(12) United States Patent
Mickley

(10) Patent No.: US 6,595,958 B1
(45) Date of Patent: Jul. 22, 2003

(54) TORTUOUS PATH INJECTION DEVICE AND METHOD

(75) Inventor: Timothy J. Mickley, Elk River, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 127 days.

(21) Appl. No.: 09/634,117

(22) Filed: Aug. 8, 2000

(51) Int. Cl.[7] .............................................. A61M 5/178
(52) U.S. Cl. .................................................. 604/164.01
(58) Field of Search ..................... 604/96.01, 164.01, 604/164.02, 164.03, 164.06, 264, 252, 258, 523, 532, 534, 171; 606/194

(56) References Cited

U.S. PATENT DOCUMENTS

| | | | |
|---|---|---|---|
| 4,578,061 A | 3/1986 | Lemelson | 604/164 |
| 4,658,817 A | 4/1987 | Hardy | 128/303.1 |
| 4,760,131 A | 7/1988 | Sundsmo et al. | 530/356 |

(List continued on next page.)

FOREIGN PATENT DOCUMENTS

| | | |
|---|---|---|
| DE | 296 09 35 U1 | 10/1996 |
| DE | 195 37 081 A1 | 4/1997 |
| EP | 0 689 467 B1 | 1/1996 |
| WO | WO 96/35469 | 11/1996 |
| WO | WO 96/39963 | 12/1996 |
| WO | WO 97/18768 | 5/1997 |
| WO | WO 97/29803 | 8/1997 |
| WO | WO 97/32551 | 9/1997 |
| WO | WO 97/44071 | 11/1997 |
| WO | WO 98/05307 | 2/1998 |
| WO | WO 98/16157 | 4/1998 |
| WO | WO 98/17186 | 4/1998 |
| WO | WO 98/18391 | 5/1998 |
| WO | WO 98/27877 | 7/1998 |
| WO | WO 98/39038 | 9/1998 |
| WO | WO 99/04850 | 2/1999 |
| WO | WO 99/04851 | 2/1999 |
| WO | WO 99/29251 | 6/1999 |
| WO | WO 99/39624 | 8/1999 |
| WO | WO 99/44656 | 9/1999 |
| WO | WO 99/49773 | 10/1999 |
| WO | WO 00/15146 | 3/2000 |
| WO | WO 00/16704 | 3/2000 |

OTHER PUBLICATIONS

Goodman et al., Synthesis and Characterization of Radio-iodinated N-( )3_Iodopropen-1-yl)-2β-carbomethoxy-3β-(4-chlorophenyl)tropanes: Potential Dopamine Reuptake Site Imaging Agents, 37 pp. 1535-1542 (1994).

Mirhoseini et al., "Transventricular Revascularization by Laser," *Lasers In Surgery and Medicine*, 2:187-198, (1982).

Gal et al., Analysis of Photoproducts, Free Radicals, and Particulate Debris Generated During In Vivo Argon Laser Myoplasty, *Lasers in Surgery and Medicine*, 11:125-132 (1991).

(List continued on next page.)

*Primary Examiner*—Manuel Mendez
*Assistant Examiner*—Mark K. Han
(74) *Attorney, Agent, or Firm*—Kenyon & Kenyon

(57) ABSTRACT

Devices and methods for delivering therapeutic or diagnostic agents to a target tissue of a human body are disclosed. A catheter in accordance with the present invention includes an elongate shaft having a distal end, a proximal end, and a lumen therethrough. The elongate shaft includes a first curved portion proximate the distal end of the elongate shaft. The first curved portion of the elongate shaft defines a first plane. The elongate shaft also includes a second curved portion disposed between the distal end of the elongate shaft and the first curved portion of the elongate shaft. The second curved portion of the elongate shaft defines a second plane. The second plane intersects the first plane at an angle.

22 Claims, 11 Drawing Sheets

U.S. PATENT DOCUMENTS

| | | | |
|---|---|---|---|
| 4,790,311 A | 12/1988 | Ruiz | 128/303.1 |
| 4,896,671 A | 1/1990 | Cunningham et al. | 128/642 |
| 4,940,458 A * | 7/1990 | Cohn | 600/561 |
| 5,047,026 A | 9/1991 | Rydell | 606/48 |
| 5,093,877 A | 3/1992 | Aita et al. | 385/34 |
| 5,221,269 A * | 6/1993 | Miller et al. | 604/170.03 |
| 5,261,889 A | 11/1993 | Laine et al. | 604/164 |
| 5,267,982 A * | 12/1993 | Sylvanowicz | 604/256 |
| 5,287,861 A | 2/1994 | Wilk | 128/898 |
| 5,353,800 A | 10/1994 | Pohndorf et al. | 128/673 |
| 5,354,279 A | 10/1994 | Hofling | 604/164 |
| 5,358,485 A | 10/1994 | Vance et al. | 604/22 |
| 5,364,393 A | 11/1994 | Auth et al. | 606/34 |
| 5,370,675 A | 12/1994 | Edwards et al. | 607/101 |
| 5,380,316 A | 1/1995 | Aita et al. | 606/7 |
| 5,389,096 A | 2/1995 | Aita et al. | 606/15 |
| 5,403,311 A | 4/1995 | Abele et al. | 606/49 |
| 5,405,376 A | 4/1995 | Mulier et al. | 607/127 |
| 5,431,649 A | 7/1995 | Mulier et al. | 606/41 |
| 5,464,395 A | 11/1995 | Faxon et al. | 604/96 |
| 5,480,389 A * | 1/1996 | McWha et al. | 604/158 |
| 5,522,815 A | 6/1996 | Durgin, Jr. et al. | 606/50 |
| 5,551,427 A | 9/1996 | Altman | 128/642 |
| 5,569,462 A | 10/1996 | Martinson et al. | 424/424 |
| 5,591,132 A * | 1/1997 | Carrie | 604/158 |
| 5,591,159 A | 1/1997 | Taheri | 606/15 |
| 5,593,405 A | 1/1997 | Osypka | 606/15 |
| 5,601,586 A | 2/1997 | Fucci et al. | 606/167 |
| 5,601,588 A | 2/1997 | Tonomura et al. | 606/185 |
| 5,607,405 A | 3/1997 | Decker et al. | 604/264 |
| 5,620,414 A | 4/1997 | Campbell, Jr. | 604/22 |
| 5,672,174 A | 9/1997 | Gough et al. | 606/41 |
| 5,681,308 A | 10/1997 | Edwards et al. | 606/41 |
| 5,683,366 A | 11/1997 | Eggers et al. | 604/114 |
| 5,697,882 A | 12/1997 | Eggers et al. | 604/114 |
| 5,700,259 A | 12/1997 | Negus et al. | 606/14 |
| 5,713,894 A | 2/1998 | Murphy-Chutorian et al. | 605/15 |
| 5,725,521 A | 3/1998 | Mueller | 606/7 |
| 5,725,523 A | 3/1998 | Mueller | 606/15 |
| 5,766,164 A | 6/1998 | Mueller et al. | 606/15 |
| 5,769,843 A | 6/1998 | Abela et al. | 604/10 |
| 5,797,870 A | 8/1998 | March et al. | 604/49 |
| 5,807,388 A | 9/1998 | Jeevanandam et al. | 606/15 |
| 5,810,836 A | 9/1998 | Hussein et al. | 606/108 |
| 5,827,203 A | 10/1998 | Nita | 601/2 |
| 5,840,059 A | 11/1998 | March et al. | 604/53 |
| 5,871,495 A | 2/1999 | Mueller | 606/185 |
| 5,873,366 A | 2/1999 | Chim et al. | 128/898 |
| 5,873,855 A | 2/1999 | Eggers et al. | 604/114 |
| 5,902,289 A | 5/1999 | Swartz et al. | |
| 5,911,729 A | 6/1999 | Shikhman et al. | 606/181 |
| 5,913,853 A | 6/1999 | Loeb et al. | 606/15 |
| 5,921,982 A | 7/1999 | Lesh et al. | 606/41 |
| 5,925,033 A | 7/1999 | Aita et al. | 606/7 |
| 5,931,848 A | 8/1999 | Saadat | 606/167 |
| 5,944,716 A | 8/1999 | Hektner | 606/45 |
| 5,947,989 A | 9/1999 | Shikhman et al. | 606/180 |
| 5,964,754 A | 10/1999 | Osypka | 606/37 |
| 6,004,280 A | 12/1999 | Buck et al. | |
| 6,042,581 A | 3/2000 | Ryan et al. | 606/45 |
| 6,045,565 A | 4/2000 | Ellis et al. | 606/167 |
| 6,053,911 A | 4/2000 | Ryan et al. | 606/33 |
| 6,053,924 A | 4/2000 | Hussein | 606/108 |
| 6,056,742 A | 5/2000 | Murphy-Chutorian et al. | 606/11 |
| 6,056,743 A | 5/2000 | Ellis et al. | 606/15 |
| 6,066,126 A | 5/2000 | Li et al. | |
| 6,068,622 A * | 5/2000 | Sater et al. | 604/524 |
| 6,203,524 B1 * | 3/2001 | Burney et al. | 128/898 |
| 6,217,554 B1 | 4/2001 | Green | |
| 6,228,049 B1 * | 5/2001 | Schroeder et al. | 128/898 |
| 6,425,887 B1 * | 7/2002 | McGuckin et al. | 604/272 |

OTHER PUBLICATIONS

Isner, J., "Right Ventricular Myocardial Infarction," *Journal of the American Medical Association,* vol. 259, No. 5, Feb. 5, 1988, 12 pages.

Pickering et al., "Proliferative Activity in Peripheral and Coronary Atherosclerotic Plaque among Patients Undergoing Percutaneous Revascularization," *The Journal of Clinical Investigation,* ISSN 0021–9738, Apr. 1993, vol. 91, pp. 1469–1480.

Vineberg et al., "Creation of Intramyocardial Pathways to Channel Oxygenated Blood Between Ventricular Arteriolar Zones: A Preliminary Report," Canadian Medical Association, vol. 96, Feb. 4, 1967.

Vineberg, A., "Results of 14 Years' Experience in the Surgical Treatment of Human Coronary Arrtery Insufficiency," Canadian Medical Association, vol. 92, Feb. 13, 1965.

Vineberg, et al. "The Ivalon Sponge Procedure For Myocardial Revascularization," *Surgery,* vol. 47, No. 2, Feb. 1960, pp. 268–289.

Vineberg et al., "Treatment of acute myocardial infarction by endocardial resection," *Surgery,* vol. 57, No. 6, Jun. 1965, pp. 832–835.

Walter et al., "Treatment of Acute Myocardial Infarction by Transmural Blood Supply from the Ventricular Cavity," *European Surgical Research,* 3:130–138 (1971).

Khazei et al., "Myocardial Canalization," *The Annals of Thoracic Surgery,* vol. 6, No. 2, Aug. 1968, pp. 163–171.

Hershey et al., Transmyocardial puncture revascularization, *Geriatrics,* Mar. 1969, pp. 101–108.

Goldman, M.L. et al., "Nonoperative Portacaval Shunt in Swine," *Investigative Radiology,* vol. 25, No. 5, May 1990.

Press Release dated Oct. 21, 1996, "Doctor's Demonstrate Proof of Blood Flow Through Open TMR Channels Created with PLC Systems CO2 Heart Laser Using New Ultrasound Device; Studies Demonstrated Correlation Between Redution in Angina Class and Myocardial Blood Flow in TMR Channels".

Press Release dated Oct. 10, 1996, "Texas Heart Institute Presents Study Comparing The Use of CO2, Holmium and Excimer Lasers for TMR; Study Shows That PLC System3 CO2 Heart Laser, Synchronized to a Beating Heart is the Safest Laser for TMR; Failure to Synchronize May Lead to an 18 Times Increase in Life Threatening Arrthmias."

Schumacher, et al. Induction of Neoagniogenesis in Ischemic Myocardium by Human Growth Factors, *Clinical Investigation and Reports,* Dec. 1, 1997, 6 pages.

Winslow, R., "Genetic Techniques Succeed in Treating Patients with Obstructed Blood Vessels," *The Wall Street Journal,* published on or before Nov. 2, 1998.

Kolata, G., "Gene Therapy Gives Blood a Path Around Leg Blockages, Researchers Say," *The New York Times,* Nov. 10, 1997.

Mack et al., "Cardiopulmonary Support and Physiology," *The Journal of Thoracic and Cardiovascular Surgery,* vol. 115, No. 1, Jan. 1998, 10 pages.

* cited by examiner

TORTUOUS PATH INJECTION DEVICE AND METHOD

RELATED APPLICATIONS

The present application is related to U.S. patent application Ser. No. 09/633,924, filed by the same assignee on even date herewith and entitled "Controlled Depth Injection Device and Method." The present application is also related to U.S. patent application Ser. No. 09/635,083, filed by the same assignee on even date herewith and entitled "Catheter Shaft Assembly."

FIELD OF THE INVENTION

The present invention relates generally to devices and methods for delivering therapeutic or diagnostic agents to a portion of the human body. More particularly, the present invention relates generally to devices and methods for delivering and injecting fluid into heart tissue.

BACKGROUND OF THE INVENTION

Injection catheters may be used to inject therapeutic or diagnostic agents into a variety of organs, such as the heart. In the case of injecting a therapeutic agent into the heart, 27 or 28 gauge needles are generally used to inject solutions carrying genes, proteins, or drugs directly into the myocardium. A typical volume of an agent delivered to an injection site is about 100 microliters. A limitation to this method of delivering therapeutic agents to the heart is that the injected fluid tends to leak from the site of the injection after the needle is disengaged from the heart. In fact, fluid may continue to leak over several seconds. In the case of dynamic organs such as the heart, there may be more pronounced leakage with each muscle contraction.

Many medical procedures involve the delivery of therapeutic and diagnostic agents to a targeted portion of a patient's body. For example, the delivery of a therapeutic agent is used in the treatment of esophageal varices, a condition where blood vessels of the esophagus are enlarged and may potentially burst. For such a procedure, a therapeutic agent is injected into the varix. When treating an esophageal varix, the agent may be a coagulant such as sodium morrhuate. When a coagulant is injected into a varix, it causes it to occlude. An injection catheter may be used to deliver the therapeutic agent in order to minimize the invasive nature of the procedure.

In a similar procedure, an injection catheter may be utilized in the treatment of ulcers in the stomach lining. With such treatment, an injection catheter may be used to deliver drugs such as sclerosing or vasoconstrictive agents. These drugs typically clot or occlude the bleeding tissue to stop bleeding or to reduce the possibility of a blood vessel bursting.

As mentioned previously, injection catheters may also be used to inject therapeutic or diagnostic agents into the heart. A limitation to this method of delivering therapeutic agents to the heart is that the injected fluid tends to leak from the site of the injection after the needle is disengaged from the heart. In fact, fluid may continue to leak over several seconds. In the case of the heart, there may be more pronounced leakage with each muscle contraction.

Therapeutic and diagnostic agents may be delivered to a portion of the heart as part of a percutaneous myocardial revascularization (PMR) procedure. PMR is a procedure which is aimed at assuring that the heart is properly oxygenated. Assuring that the heart muscle is adequately supplied with oxygen is critical to sustaining the life of a patient. To receive an adequate supply of oxygen, the heart muscle must be well perfused with blood. In a healthy heart, blood perfusion is accomplished with a system of blood vessels and capillaries. However, it is common for the blood vessels to become occluded (blocked) or stenotic (narrowed). A stenosis may be formed by an atheroma which is typically a harder, calcified substance which forms on the walls of a blood vessel.

Historically, individual stenotic lesions have been treated with a number of medical procedures including coronary bypass surgery, angioplasty, and atherectomy. Coronary bypass surgery typically involves utilizing vascular tissue from another part of the patient's body to construct a shunt around the obstructed vessel. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guidewire and a balloon catheter. In these procedures, a balloon catheter is advanced over a guidewire such that the balloon is positioned proximate a restriction in a diseased vessel. The balloon is then inflated and the restriction in the vessel is opened. A third technique which may be used to treat a stenotic lesion is atherectomy. During an atherectomy procedure, the stenotic lesion is mechanically cut or abraded away from the blood vessel wall.

Coronary by-pass, angioplasty, and atherectomy procedures have all been found effective in treating individual stenotic lesions in relatively large blood vessels. However, the heart muscle is perfused with blood through a network of small vessels and capillaries. In some cases, a large number of stenotic lesions may occur in a large number of locations throughout this network of small blood vessels and capillaries. The tortuous path and small diameter of these blood vessels limit access to the stenotic lesions. The sheer number and small size of these stenotic lesions make techniques such as cardiovascular by-pass surgery, angioplasty, and atherectomy impractical When techniques which treat individual lesion are not practical percutaneous myocardial revascularization (PMR) may be used to improve the oxygenation of the myocardial tissue. A PMR procedure generally involves the creation of holes, craters or channels directly into the myocardium of the heart. In a typical PMR procedure, these holes are created using radio frequency energy delivered by a catheter having one or more electrodes near its distal end. After the wound has been created, therapeutic agents are sometimes injected into the heart chamber from the distal end of a catheter.

Positive clinical results have been demonstrated in human patients receiving PMR treatments. These results are believed to be caused in part by blood flowing within a heart chamber through channels in myocardial tissue formed by PMR. Increased blood flow to the myocardium is also believed to be caused in part by the healing response to wound formation. Specifically, the formation of new blood vessels is believed to occur in response to the newly created wound. This response is sometimes referred to as angiogenesis. After the wound has been created, therapeutic agents which are intended to promote angio-genesis are sometimes injected into the heart chamber. A limitation of this procedure is that the therapeutic agent may be quickly carried away by the flow of blood through the heart.

In addition to promoting increased blood flow, it is also believed that PMR improves a patient's condition through denervation. Denervation is the elimination of nerves. The creation of wounds during a PMR procedure results in the elimination of nerve endings which were previously sending pain signals to the brain as a result of hibernating tissue.

SUMMARY OF THE INVENTION

The present invention relates generally to devices and methods for delivering therapeutic or diagnostic agents to a portion of the human body. More particularly, the present invention relates generally to devices and methods for delivering and injecting fluid into heart tissue.

A catheter in accordance with the present invention includes a first elongate shaft having a distal end, a proximal end, and a lumen therethrough. The first elongate shaft includes a first curved portion proximate the distal end of the first elongate shaft. In a preferred embodiment, the radius of the first curved portion of the first elongate shaft is selected so that the distal end of the first elongate shaft will be disposed within a wall of an organ (e.g., the heart) during an injection procedure in accordance with a method of the present invention. The first curved portion of the first elongate shaft defines a first plane.

In one embodiment of the invention, the first elongate shaft also includes a second curved portion disposed between the distal end of the first elongate shaft and the first curved portion of the first elongate shaft. The second curved portion of the first elongate shaft defines a second plane which intersects the first plane at an angle. In a preferred embodiment, the second plane is substantially orthogonal to the first plane. This arrangement reduces the likelihood that the distal end of the first elongate shaft will perforate the wall of an organ (e.g., the heart) during an injection procedure in accordance with a method of the present invention.

In one embodiment of the present invention, a second elongate shaft is slidingly disposed within the lumen of the first elongate shaft. In this embodiment, the second elongate shaft may include a curve defining a third plane. In a preferred embodiment, the third plane is substantially orthogonal to the first plane. This arrangement reduces the likelihood that the distal end of the second elongate shaft will perforate the wall of an organ (e.g., the heart) during an injection procedure in accordance with a method of the present invention.

During an injection procedure in accordance with a method of the present invention both the first elongate shaft and the second elongate shaft may be advanced into a target tissue. After the injection of fluid into the target tissue, the first elongate shaft and the second elongate shaft may be withdrawn from the target tissue. In a preferred embodiment, the first elongate shaft and the second elongate shaft each include a plurality of curves. The tortuous path defined by the first elongate shaft and the second elongate shaft reduce the likelihood that injected fluid will escape from the target tissue after the first elongate shaft and the second elongate shaft are disengaged from the target tissue.

DETAILED DESCRIPTION OF THE INVENTION

The following detailed description should be read with reference to the drawings, in which like elements in different drawings are numbered in like fashion. The drawings, which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives which may be utilized.

Figure 1:
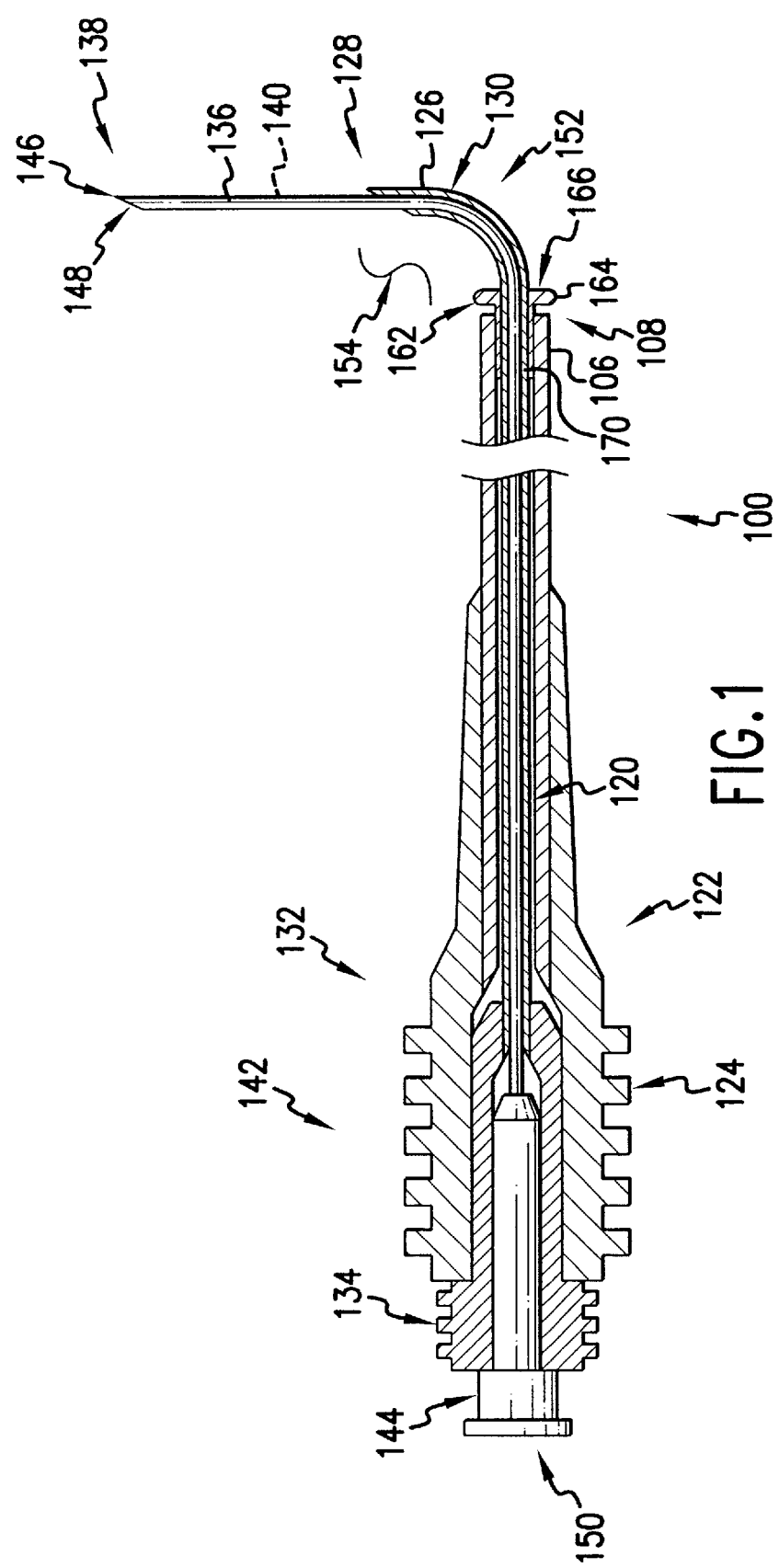
FIG. 1 is a cross sectional view of a catheter in accordance with an exemplary embodiment of the present invention.

FIG. 1 is a cross sectional view of a catheter 100 in accordance with the present invention. Catheter 100 has a distal end 102, a proximal end 104, and a sheath 106. Sheath 106 of catheter 100 includes a distal end 108 and a proximal end 122. A sheath housing 124 is disposed about sheath 106 proximate proximal end 122 thereof. Sheath 106 defines a sheath lumen 120 extending between distal end 108 and proximal end 122.

In the embodiment of FIG. 1, a first elongate shaft 126 is slidingly disposed within sheath lumen 120 of sheath 106. First elongate shaft 126 has a distal end 128, a proximal end 132, and a first shaft lumen 130 extending therebetween. A first hub 134 is disposed about first elongate shaft 126 proximate proximal end 132 thereof. A second elongate shaft 136 is slidingly disposed within first shaft lumen 130 of first elongate shaft 126. Second elongate shaft 136 has a distal end 138 and a proximal end 142. In the embodiment of FIG. 1, second elongate shaft 136 forms a point 146 proximate distal end 138 thereof. Second elongate shaft also defines an injection port 148 proximate point 146. A second hub 144 is disposed about second elongate shaft 136 proximate proximal end 142 thereof. Second hub 144 defines a proximal port 150. In a preferred embodiment, proximal port 150 is in fluid communication with injection port 148 via an injection lumen 140 defined by second elongate shaft 136.

In FIG. 1 it may be appreciated that first elongate shaft 126 includes a first curved portion 152 disposed proximate distal end 128 thereof. In the embodiment of FIG. 1, first curved portion 152 of first elongate shaft 126 defines a first plane 154 which is generally coplanar with the plane of FIG. 1.

In the embodiment of FIG. 1 a barrel 162 is partially disposed within sheath lumen 120 of sheath 106. In a preferred embodiment, barrel 162 includes a radial enlargement 164. In this preferred embodiment, radial enlargement 164 provides a generally enlarged distal contact area 166. Generally enlarged distal contact area 166 reduces the likelihood that undesired tissue damage will occur when distal end 102 of catheter 100 is urged against bodily tissue. Barrel 162 also defines a barrel lumen 170. As shown in FIG. 1, first elongate shaft 126 is slidingly disposed within barrel lumen 170.

In a preferred embodiment, first elongate shaft 126 and second elongate shaft 136 of catheter 100 comprise hypodermic tubing. First elongate shaft 126 and second elongate shaft 136 may comprise various metallic and non-metallic materials without deviating from the spirit and scope of the present invention. Examples of metallic materials which may be suitable in some applications include stainless steel, and nickel-titanium alloy. Examples of non-metallic materials which may be suitable in some applications are included in the list below, which is not exhaustive: polycarbonate, poly(L-lactide) (PLLA), poly(D,L-lactide) (PLA), polyglycolide (PGA), poly(L-lactide-co-D,L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly (phosphate ester), poly(amino acid), poly(hydroxy butyrate), polyacrylate, polyacrylamide, poly(hydroxyethyl methacrylate), polyurethane, polysiloxane and their copolymers.

In a preferred embodiment, sheath 106 of catheter 100 comprises an elongate tubular member including a reinforcement member (e.g., braided or coiled wire). Sheath 106 may comprise various metallic and non-metallic materials without deviating from the spirit and scope of the present invention. Examples of metallic materials which may be suitable in some applications include stainless steel, and nickel-titanium alloy. Examples of non-metallic materials which may be suitable in some applications include: polyethylene (PE), polypropylene (PP), polyvinylchloride (PVC), polyurethane, polytetrafluoroethylene (PTFE), polyether block amide (PEBA), polyamide, and polyimide.

Figure 2:
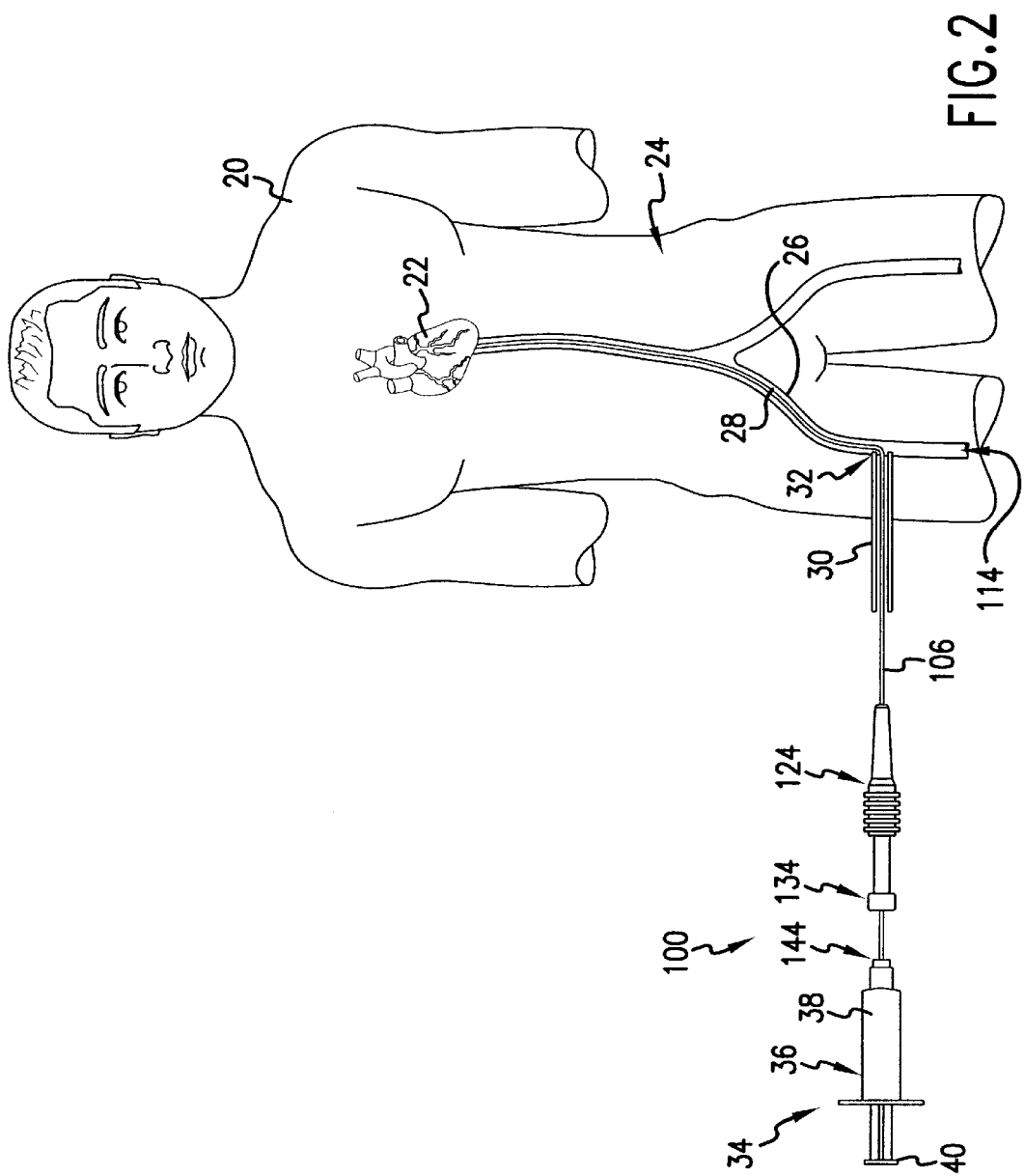
FIG. 2 is a diagrammatic view including the catheter of FIG. 1 and a patient having a heart and a vascular system including a blood vessel.

FIG. 2 is a diagrammatic view including catheter 100 of FIG. 1 and a patient 20. Patient 20 has a heart 22 and a vascular system 24 including a blood vessel 26 defining a blood vessel lumen 28. An access sheath 30 is partially disposed within a leg of patient 20. A distal end 32 of access sheath 30 is disposed within blood vessel lumen 28 of blood vessel 26. Access sheath 30 may aid in the introduction of catheter 100 into blood vessel lumen 28.

As shown in FIG. 2, a portion of catheter 100 is disposed within blood vessel lumen 28 of blood vessel 26. Distal end 102 (not visible in FIG. 2) of catheter 100 is disposed within heart 22 of patient 20. In a preferred embodiment, distal end 102 of catheter 100 is disposed proximate a wall of heart 22.

In the embodiment of FIG. 2, a fluid source 34 is coupled to second hub 144 disposed about second elongate shaft 136 of catheter 100. In the embodiment of FIG. 2, fluid source 34 includes a variable volume chamber 36 defined by a body 38. In a preferred embodiment, variable volume chamber 36 is in fluid communication with injection lumen 140 of second elongate shaft 136. A plunger 40 is slidingly disposed within variable volume chamber 36. Urging the plunger distally has the effect of urging fluid into injection lumen 140 of second elongate shaft 136. A number of energy sources may be utilized to urge plunger 40 distally. Energy sources which may be suitable in some applications include springs, compressed gas, a human being, and electricity. Various additional embodiments of fluid source 34 are possible without deviating from the spirit and scope of the present invention. Examples of fluid sources which may be suitable in some applications include syringes, peristaltic pumps, and an I.V. bag with pressure applied to its outer surface.

A method of injecting a fluid into heart 22 of patient 20 may be described with reference to FIG. 2. The distal end of access sheath 30 may be inserted into blood vessel lumen 28 of blood vessel 26. Distal end 102 of catheter 100 may be inserted into the lumen of access sheath 30. Distal end 102 of catheter 100 may be advanced through access sheath 30 and into blood vessel lumen 28 of blood vessel 26. Catheter 100 may be urged forward through vascular system 24 of patient 20 until distal end 102 is proximate the target tissue (e.g., a wall of heart 22). In FIG. 2 it may be appreciated that catheter 100 is bent in a plurality of locations to conform with a tortuous path defined by vascular system 24.

In a preferred method, distal end 138 of second elongate shaft 136 and distal end 128 of first elongate shaft 126 are disposed within sheath lumen 120 of sheath 106 during the above steps. For example, distal end 128 of first elongate shaft 126 may be pulled into sheath lumen 120 of sheath 106 urging first hub 134 proximally with respect to sheath housing 124. In a similar fashion, distal end 138 of second elongate shaft 136 may be pulled into first shaft lumen 130 of first elongate shaft 126 by urging second hub 144 proximally with respect to first hub 134.

Once distal end 102 of catheter 100 is positioned proximate the target tissue, first elongate shaft 126 may be advanced so that distal end 128 penetrates the bodily tissue at the target site. A physician may, for example, apply a distally directed force to first hub 134 to urge first elongate shaft 126 distally. Second elongate shaft 136 may also be urged distally in concert with first elongate shaft 126. In a preferred embodiment, first curved portion 152 of first elongate shaft assumes a generally curved shape when it is urged distally out of sheath lumen 120.

Second elongate shaft 136 may be advanced so that point 146 penetrates the bodily tissue proximate distal end 128 of first elongate shaft 126. In a preferred method, second elongate shaft will be advanced until injection port 148 is disposed within the target tissue. With injection port 148 of second elongate shaft 136 disposed within the target tissue, fluid may be urged into the target tissue. For example, force may be applied to plunger 40 urging fluid out of fluid source 34 and into injection lumen 140 of second elongate shaft 136. The addition of fluid from fluid source 34 results in the injection of fluid into the target tissue.

After the injection of fluid, first elongate shaft 126 and second elongate shaft 136 may be withdrawn from the target tissue. In a preferred embodiment, the tortuous path taken by first elongate shaft 126 and second elongate shaft 136 reduce the likelihood that injected fluid will escape from the target tissue after first elongate shaft 126 and second elongate shaft 136 are disengaged from the target tissue. Embodiments of catheter 100 have been envisioned in which first elongate shaft 126 and second elongate shaft 136 both include a plurality of curved portions.

Figure 3:
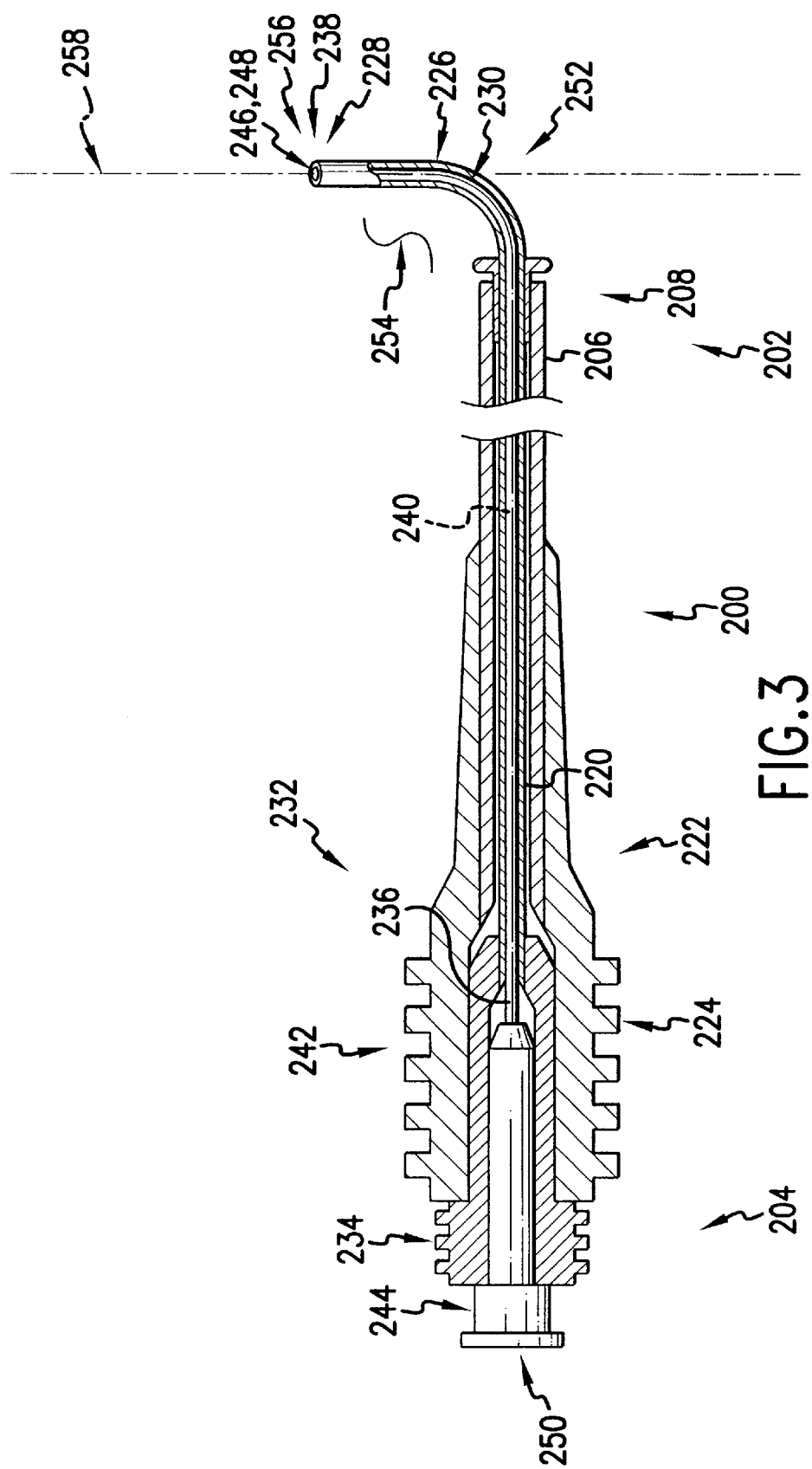
FIG. 3 is a cross sectional view of a catheter in accordance with an exemplary embodiment of the present invention.

FIG. 3 is a cross sectional view of an additional embodiment of a catheter 200 in accordance with the present invention. Catheter 200 has a distal end 202, a proximal end 204, and a sheath 206. Sheath 206 of catheter 200 includes a distal end 208, a proximal end 222. A sheath housing 224 is disposed about sheath 206 proximate proximal end 222 thereof. Sheath 206 defines a sheath lumen 220 extending between distal end 208 and proximal end 222.

In the embodiment of FIG. 3, a first elongate shaft 226 is slidingly disposed within sheath lumen 220 of sheath 206. First elongate shaft 226 has a distal end 228, a proximal end 232, and a first shaft lumen 230 extending therebetween. A first hub 234 is disposed about first elongate shaft 226 proximate proximal end 232 thereof. A second elongate shaft 236 is slidingly disposed within first shaft lumen 230 of first elongate shaft 226. Second elongate shaft 236 has a distal end 238 and a proximal end 242. In the embodiment of FIG. 3, second elongate shaft 236 forms a point 246 proximate distal end 238 thereof. Second elongate shaft defines an injection port 248 proximate point 246. A second hub 244 is disposed about second elongate shaft 236 proximate proximal end 242 thereof Second hub 244 defines a proximal port 250. In a preferred embodiment, proximal port 250 is in fluid communication with injection port 248 via an injection lumen 240 defined by second elongate shaft 236.

In FIG. 3 it may be appreciated that first elongate shaft 226 includes a first curved portion 252 disposed proximate distal end 228 thereof. In the embodiment of FIG. 3, first curved portion 252 of first elongate shaft 226 defines a first plane 254 which is generally coplanar with the plane of FIG. 3. First elongate shaft 226 also includes a second curved portion 256 defining a second plane 258. In the embodiment of FIG. 3, second plane 258 is substantially orthogonal to first plane 254.

Figure 4:
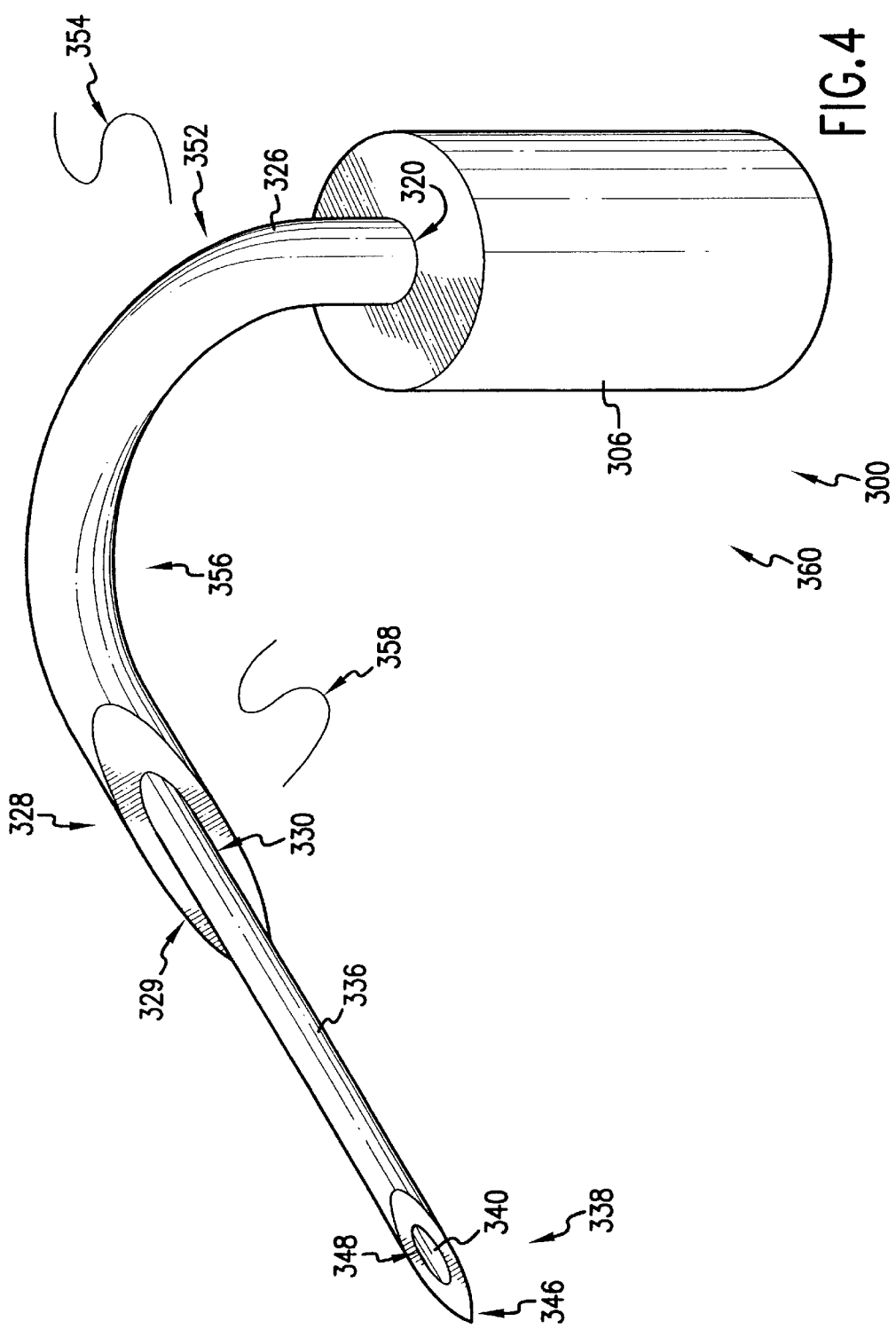
FIG. 4 is a perspective view of a distal portion of a catheter in accordance with an exemplary embodiment of the present invention.

FIG. 4 is a perspective view of a distal portion 360 of an additional embodiment of a catheter 300 in accordance with the present invention. Catheter 300 includes a sheath 306 defining a sheath lumen 320. A first elongate shaft 326 is partially disposed within sheath lumen 320 of sheath 306. First elongate shaft 326 includes a first curved portion 352 defining a first plane 354 and a second curved portion 356 defining a second plane 358 disposed proximate a distal end 328 thereof. In FIG. 4 it may also be appreciated that first elongate shaft 326 forms a point 329 proximate distal end 328 thereof.

Catheter 300 also includes a second elongate shaft 336 which is partially disposed in a first shaft lumen 330 defined by first elongate shaft 326. Second elongate shaft 336 defines an injection lumen 340 and an injection port 348. Second elongate shaft 336 also forms a point 346 proximate a distal end 338 thereof.

Figure 5:
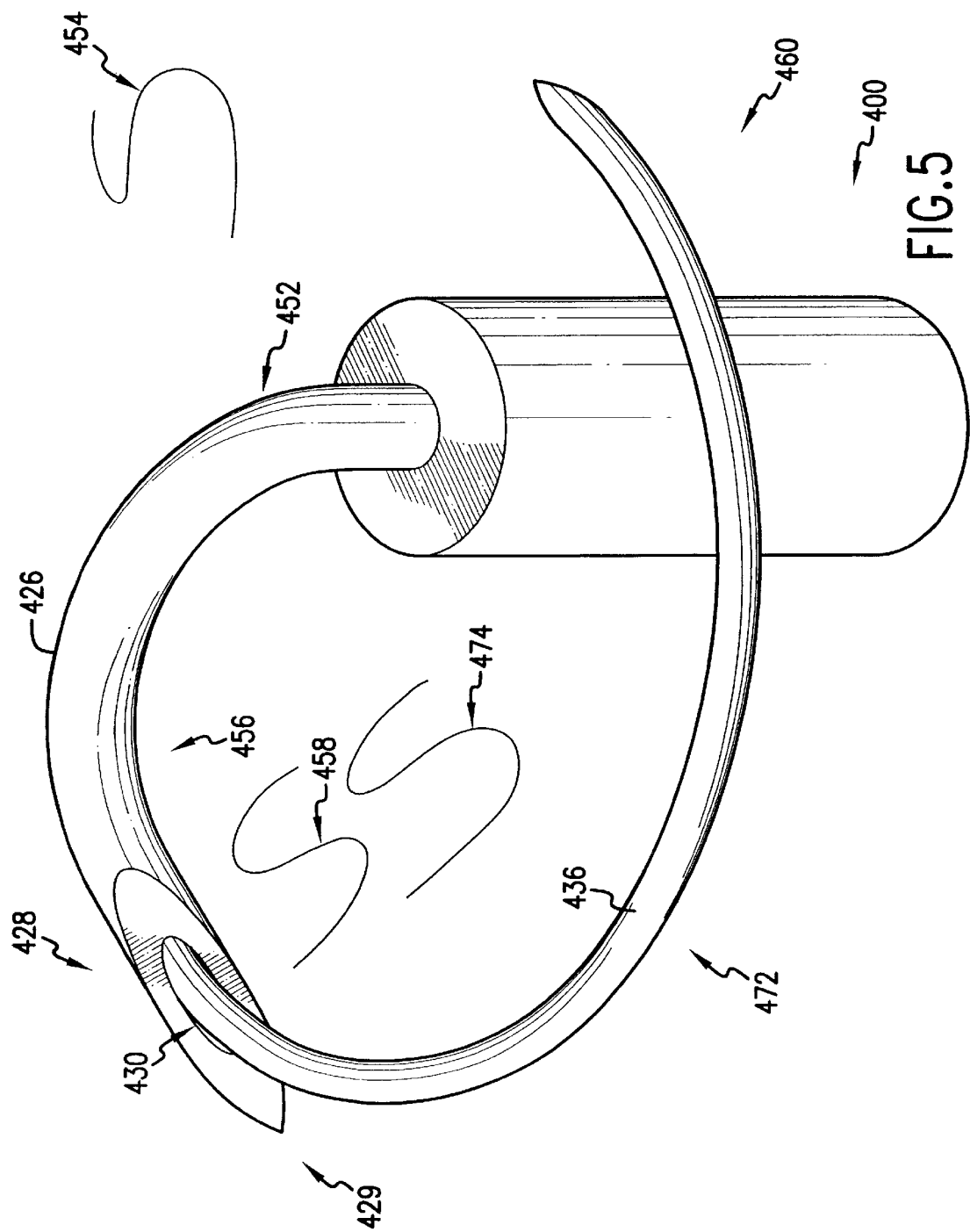
FIG. 5 is a perspective view of a distal portion of a catheter in accordance with an exemplary embodiment of the present invention.

FIG. 5 is a perspective view of a distal portion 460 of an additional embodiment of a catheter 400 in accordance with the present invention. Catheter 400 includes a second elongate shaft 436 having a curved portion 472. A portion of second elongate shaft 436 is disposed within a first lumen 430 defined by a first elongate shaft 426. First elongate shaft 426 includes a first curved portion 452 and a second curved portion 456. In FIG. 5 it may also be appreciated that first elongate shaft 426 forms a point 429 proximate distal end 428 thereof.

In the embodiment of FIG. 5, first curved portion 452 of first elongate shaft 426 defines a first plane 454 and second curved portion of first elongate shaft 426 defines a second plane 458. Also in the embodiment of FIG. 5, curved portion 472 of second elongate shaft 436 defines a third plane 474. In the embodiment of FIG. 5, second plane 458 is substantially orthogonal to first plane 454. Also in the embodiment of FIG. 5, third plane 474 is generally co-planar with second plane 458. In a preferred embodiment, curved portion 472 is biased to return to the shape illustrated in FIG. 5. In this preferred embodiment, curved portion 472 of second elongate shaft 436 may tend to self-align with second curved portion 456 of first elongate shaft 426. In a particularly preferred embodiment, the radius of curved portion 472 of second elongate shaft 436 is substantially equal to the radius of second curved portion 456 of first elongate shaft 426.

In a preferred embodiment, the radius of first curved portion 452 of first elongate shaft 426 is selected so that distal end 428 of first elongate shaft 426 will be disposed within a wall of an organ (e.g., the heart) during an injection procedure in accordance with a method of the present invention. Also in a preferred embodiment, third plane 474 defined by curved portion 472 of second elongate shaft 436 is substantially orthogonal to first plane 454 defined by first curved portion 452 of first elongate shaft 426. This relationship reduces the likelihood that the distal end of second elongate shaft 436 will perforate the wall of an organ (e.g., the heart) during an injection procedure in accordance with a method of the present invention.

In a preferred embodiment the radius of first curved portion 452 of first elongate shaft 426 is, for example, between about 1.0 and about 10.0 millimeters. In a particularly preferred embodiment the radius of first curved portion 452 of first elongate shaft 426 is, for example, between about 3.0 and about 7.0 millimeters.

In a preferred embodiment the radius of second curved portion 456 of first elongate shaft 426 is, for example, between about 1.0 and about 8.0 millimeters. In a particularly preferred embodiment the radius of second curved portion 456 of first elongate shaft 426 is, for example, between about 2.0 and about 5.0 millimeters.

In a preferred embodiment the radius of curved portion 472 of second elongate shaft 436 is, for example, between about 1.0 and about 8.0 millimeters. In a particularly preferred embodiment the radius of curved portion 472 of second elongate shaft 436 is, for example, between about 2.0 and about 5.0 millimeters.

Embodiments of catheter 400 have been envisioned in which first elongate shaft 426 and second elongate shaft 436 both include a plurality of curved portions. In a preferred embodiment, the tortuous path taken by first elongate shaft 426 and second elongate shaft 436 reduces the likelihood that fluid will escape from a target tissue after it has been injected therein.

It is to be appreciated that the radius of curved portion 472 may vary along the length of second elongate shaft 436. Likewise, it is to be appreciated that the radius of first curved portion 452 and second curved portion 456 may vary along the length of first elongate shaft 426. To explain further, a curve of constant radius forms a portion of a circle whereas a curve of variable radius may form a portion of a spiral. First elongate shaft 426 and second elongate shaft 436 both may include a plurality of curved portions having various shapes. Embodiments of the present invention have been envisioned in which the injection path includes a plurality of turns. These turns may be any shape. Examples of turn shapes which may be suitable in some applications include circular arcs and spiral arcs. Embodiments of the present invention have also been envisioned in which the injection path is generally in the shape of a helix having an expanding radial pitch.

Figure 6:
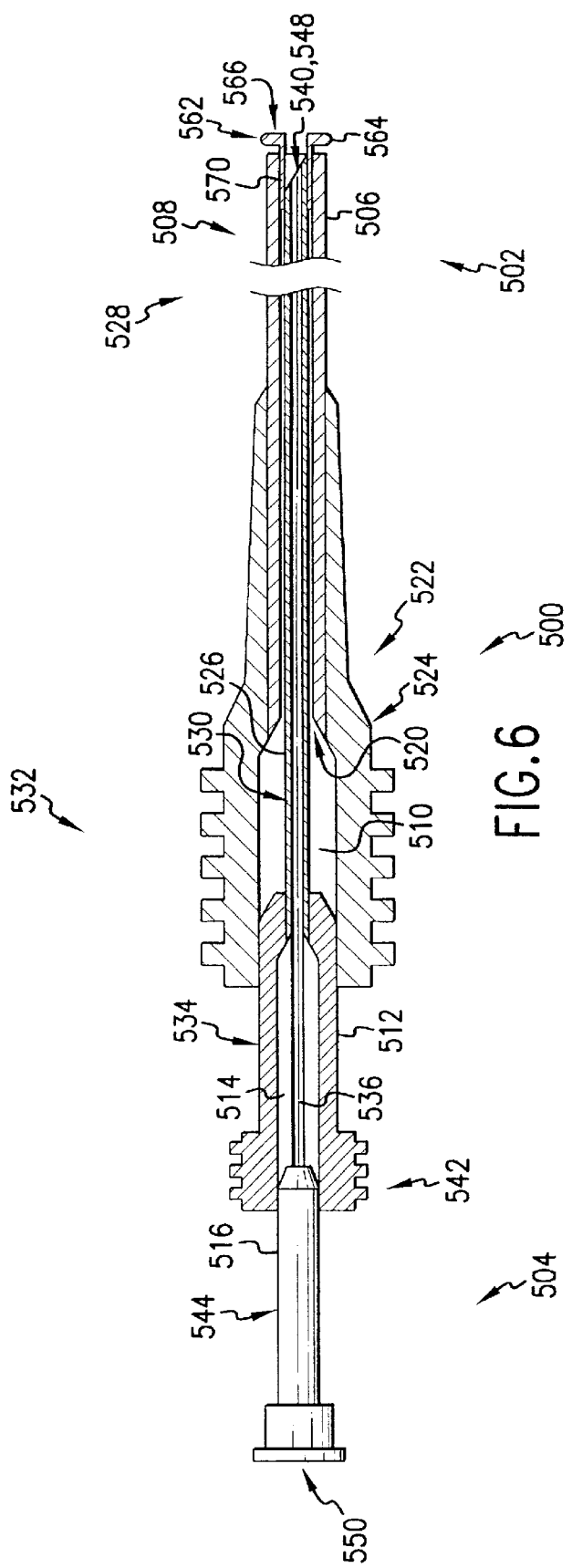
FIG. 6 is a cross sectional view of a catheter in accordance with an exemplary embodiment of the present invention.

FIG. 6 is a cross sectional view of an additional embodiment of a catheter 500 in accordance with the present invention. Catheter 500 has a distal end 502, a proximal end 504, and a sheath 506. Sheath 506 of catheter 500 includes a distal end 508 and a proximal end 522. A sheath housing 524 is disposed about sheath 506 proximate proximal end 522 thereof. Sheath 506 defines a sheath lumen 520 extending between distal end 508 and proximal end 522.

In the embodiment of FIG. 6, a first elongate shaft 526 is slidingly disposed within sheath lumen 520 of sheath 506. First elongate shaft 526 has a distal end 528, a proximal end 532, and a first shaft lumen 530 extending therebetween. A first hub 534 is disposed about first elongate shaft 526 proximate proximal end 532 thereof.

A second elongate shaft 536 is slidingly disposed within first shaft lumen 530 of first elongate shaft 526. A second hub 544 is disposed about second elongate shaft 536 proximate a proximal end 542 thereof. Second hub 544 defines a proximal port 550. In a preferred embodiment, proximal port 550 is in fluid communication with an injection lumen 540 and an injection port 548 defined by second elongate shaft 536.

In the embodiment of FIG. 6 a barrel 562 is partially disposed within sheath lumen 520 of sheath 506. In a preferred embodiment, barrel 562 includes a radial enlargement 564. In this preferred embodiment, radial enlargement 564 provides a generally enlarged distal contact area 566. Generally enlarged distal contact area 566 reduces the likelihood that undesired tissue damage will occur when distal end 502 of catheter 500 is urged against bodily tissue. Barrel 562 also defines a barrel lumen 570. As shown in FIG. 6, first elongate shaft 526 is slidingly disposed within barrel lumen 570.

As shown in FIG. 6, sheath housing 524 defines a first guiding surface 510. First hub 534 has a first mating surface 512 and a second guiding surface 514. First mating surface 512 of first hub 534 is disposed in sliding engagement with first guiding surface 510 of sheath housing 524. In a similar fashion, a second mating surface 516 of second hub 544 is disposed in sliding engagement with second guiding surface 514 of first hub 534.

In the embodiment of FIG. 6, first elongate shaft 526 and second elongate shaft 536 are biased to assume curved shapes. In the embodiment of FIG. 6, first elongate shaft 526 and second elongate shaft 536 have been urged proximally so that their respective distal ends are disposed within sheath lumen 520 of sheath 506. In FIG. 6 it may be appreciated that first elongate shaft 526 and second elongate shaft 536 have been urged into a substantially straight position. In a preferred embodiment, first elongate shaft 526 and second elongate shaft 536 will return to substantially curved shapes when they are urged distally out of sheath lumen 520.

When first elongate shaft 526 and second elongate shaft 536 are advanced into a target tissue, injection lumen 540 of second elongate shaft 536 will define a tortuous injection path. The tortuous injection path defined by injection lumen 540 of second elongate shaft 536 may be described utilizing cylindrical coordinates. Cylindrical coordinates are an extension of two dimensional polar coordinates to include a third or longitudinal dimension Z.

An exemplary tortuous injection path is described in table 1. The first column of table 1 is the linear distance Z which the tortuous injection path extends beyond distal contact area 566 of catheter 500. The second column in table 1 is the radial distance R in millimeters from the longitudinal axis of barrel lumen 570 of barrel 562 of catheter 500. The third column of table 1 is an angular dimension φ measured about the longitudinal axis of barrel lumen 570 of barrel 562 of catheter 500.

TABLE 1

| Z [mm] | R [mm] | φ [degrees] |
|---|---|---|
| 0 | 0 | 0 |
| 1.0 | 1.0 | 0 |
| 1.5 | 1.5 | 0 |
| 2.0 | 2.0 | 0 |
| 2.5 | 2.0 | 0 |
| 2.5 | 2.2 | 30 |
| 2.5 | 2.5 | 60 |
| 2.5 | 3.0 | 90 |
| 5.0 | 4.0 | 120 |
| 5.0 | 4.0 | 150 |
| 5.0 | 4.0 | 180 |
| 7.5 | 6.0 | 210 |
| 7.5 | 6.0 | 240 |
| 7.5 | 6.0 | 270 |
| 10.0 | 8.0 | 300 |
| 10.0 | 8.0 | 330 |
| 10.0 | 8.0 | 360 |

Figure 7:
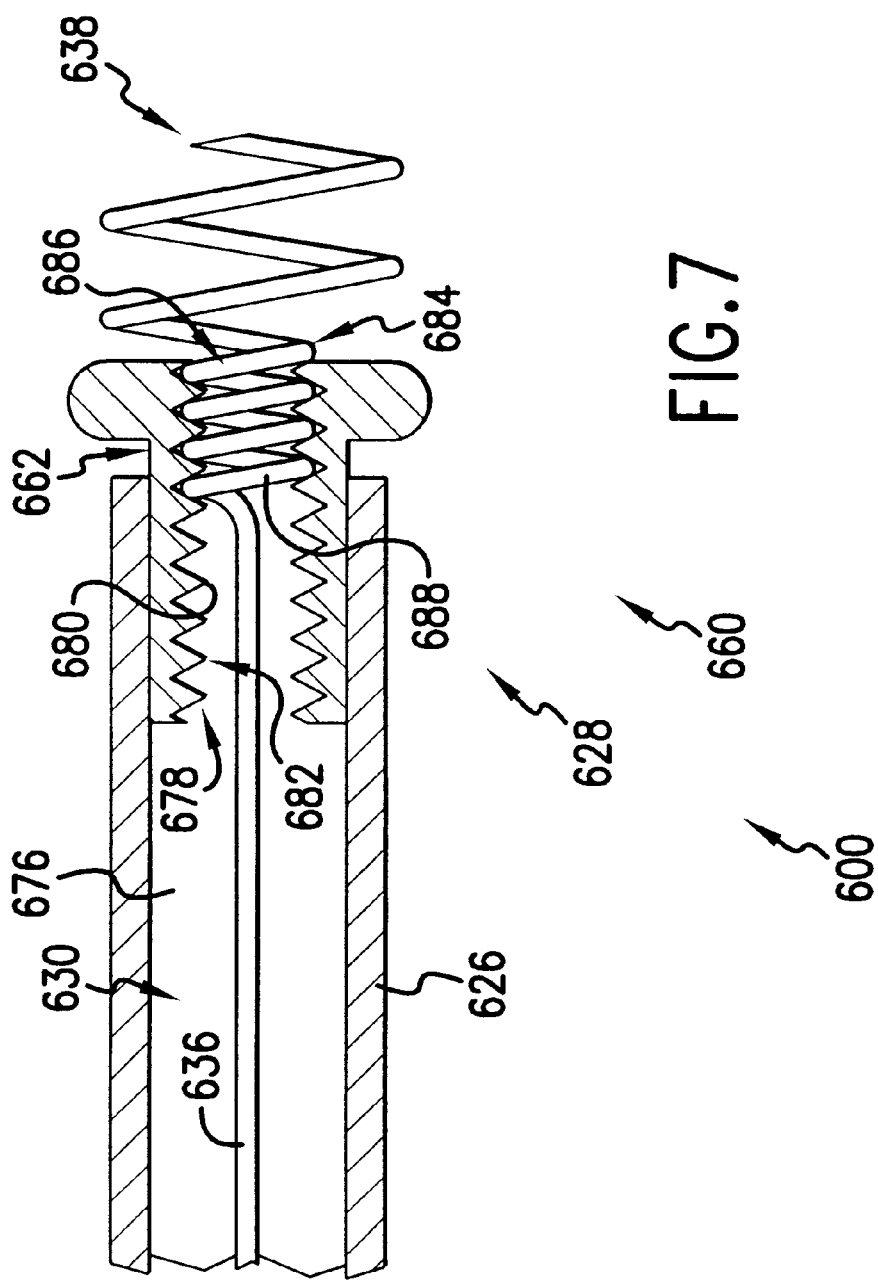
FIG. 7 is a partial cross sectional view of a distal portion of a catheter in accordance with an exemplary embodiment of the present invention.

FIG. 7 is a partial cross sectional view of a distal portion 660 of an additional embodiment of a catheter 600 in accordance with the present invention. Catheter 600 includes a first elongate shaft 626 having a distal end 628 and an inside surface 676 defining a first shaft lumen 630. A barrel 662 is partially disposed within first shaft lumen 630 of first elongate shaft 626 proximate distal end 628. Barrel 662 includes a first helical member 678 comprising a plurality of turns 680. In the embodiment of FIG. 7, first helical member 678 comprises a first screw thread 682.

A second elongate shaft 636 is partially disposed within first shaft lumen 630 of first elongate shaft 626. Second elongate shaft 636 forms a second helical member 684. In the embodiment of FIG. 7, second helical member 684 comprises a coil 686 having a plurality of turns 688. In FIG. 7, it may be appreciated that a plurality of turns 688 of second helical member 684 are disposed between a plurality of turns 680 of first helical member 678. Also in FIG. 7, it may be appreciated that second helical member 684 is biased to expand in diameter. A distal end 638 of second elongate shaft 636 may be advanced into a target tissue by rotating second elongate shaft 636.

Figure 8:
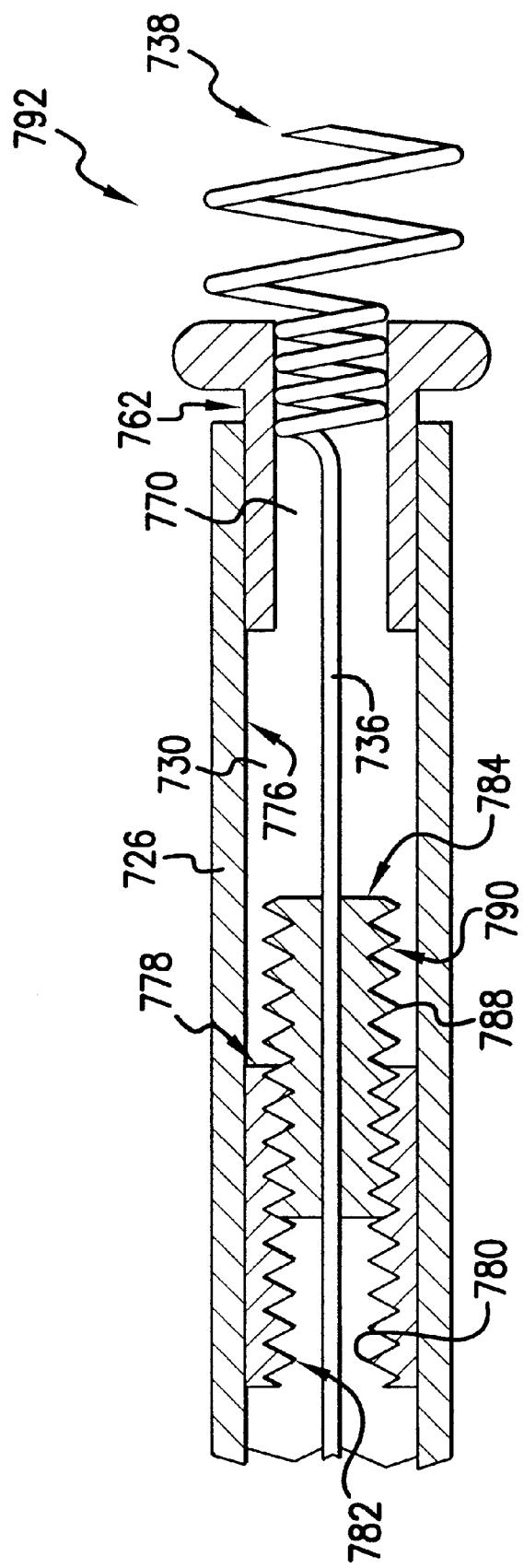
FIG. 8 is a partial cross sectional view of a distal portion of a catheter in accordance with an exemplary embodiment of the present invention.

FIG. 8 is a partial cross sectional view of a distal portion 760 of an additional embodiment of a catheter 700 in accordance with the present invention. In FIG. 8 it may be appreciated that catheter 700 includes a first helical member 778 comprising a plurality of turns 780 disposed within a first shaft lumen 730 defined by an inside surface 776 of a first elongate shaft 726. In a preferred embodiment, first helical member 778 is fixed to inside surface 776 of first elongate shaft 726. In the embodiment of FIG. 8, first helical member 778 comprises a first screw thread 782.

Also in the embodiment of FIG. 8, a second helical member 784 comprising a plurality of turns 788 is disposed about a second elongate shaft 736. In the embodiment of FIG. 8, second helical member 784 is preferably fixed to second elongate shaft 736. In the embodiment of FIG. 8, second helical member 784 comprises a second screw thread 790. In FIG. 8, it may be appreciated that a plurality of turns 788 of second helical member 784 are disposed between a plurality of turns 780 of first helical member 778.

In the embodiment of FIG. 8, a barrel 762 defining a barrel lumen 770 is partially disposed within first shaft lumen 730 of first elongate shaft 726. A coiled portion 792 of second elongate shaft 736 is disposed within barrel lumen 770 of barrel 762. In FIG. 8, it may be appreciated that coiled portion 792 is biased to expand in diameter. A distal end 738 of second elongate shaft 736 may be advanced into a target tissue by rotating second elongate shaft 736.

Figure 9:
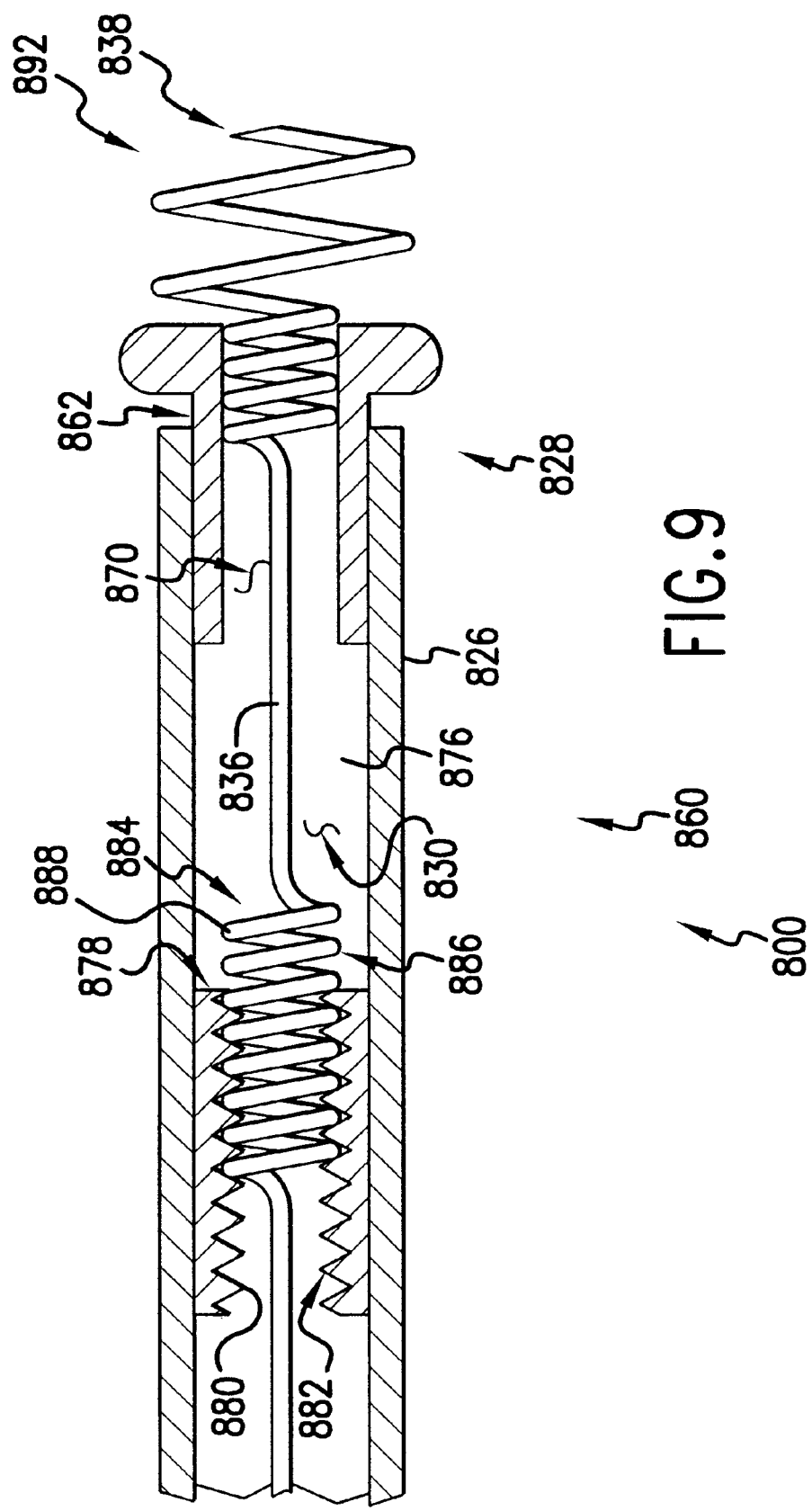
FIG. 9 is a partial cross sectional view of a distal portion of a catheter in accordance with an exemplary embodiment of the present invention.

FIG. 9 is a partial cross sectional view of a distal portion 860 of an additional embodiment of a catheter 800 in accordance with the present invention. Catheter 800 includes a first elongate shaft 826 having a distal end 828 and an inside surface 876 defining a first shaft lumen 830. Catheter 800 also includes a second elongate shaft 836 having a distal end 838 slidingly disposed within first shaft lumen 830 of first elongate shaft 826.

In FIG. 9 it may be appreciated that catheter 800 includes a first helical member 878 comprising a plurality of turns 880 disposed within first shaft lumen 830 of first elongate shaft 826. In a preferred embodiment, first helical member 878 is fixed to an inside surface 876 of first elongate shaft 826. In the embodiment of FIG. 9, first helical member 878 comprises a first screw thread 882.

A second helical member 884 is formed by second elongate shaft 836. In the embodiment of FIG. 9, second helical member 884 comprises a coil 886 having a plurality of turns 888. In FIG. 9, it may be appreciated that a plurality of turns 888 of second helical member 884 are disposed between a plurality of turns 880 of first helical member 878. Embodiments of the present invention have also been envisioned in which first helical member 878 comprises a coil.

In the embodiment of FIG. 9, a barrel 862 defining a barrel lumen 870 is partially disposed within first shaft lumen 830 of first elongate shaft 826. A coiled portion 892 of second elongate shaft 836 is disposed within barrel lumen 870 of barrel 862. In FIG. 9, it may be appreciated that coiled portion 892 is biased to expand in diameter. A distal end 838 of second elongate shaft 836 may be advanced into a target tissue by rotating second elongate shaft 836.

Figure 10:
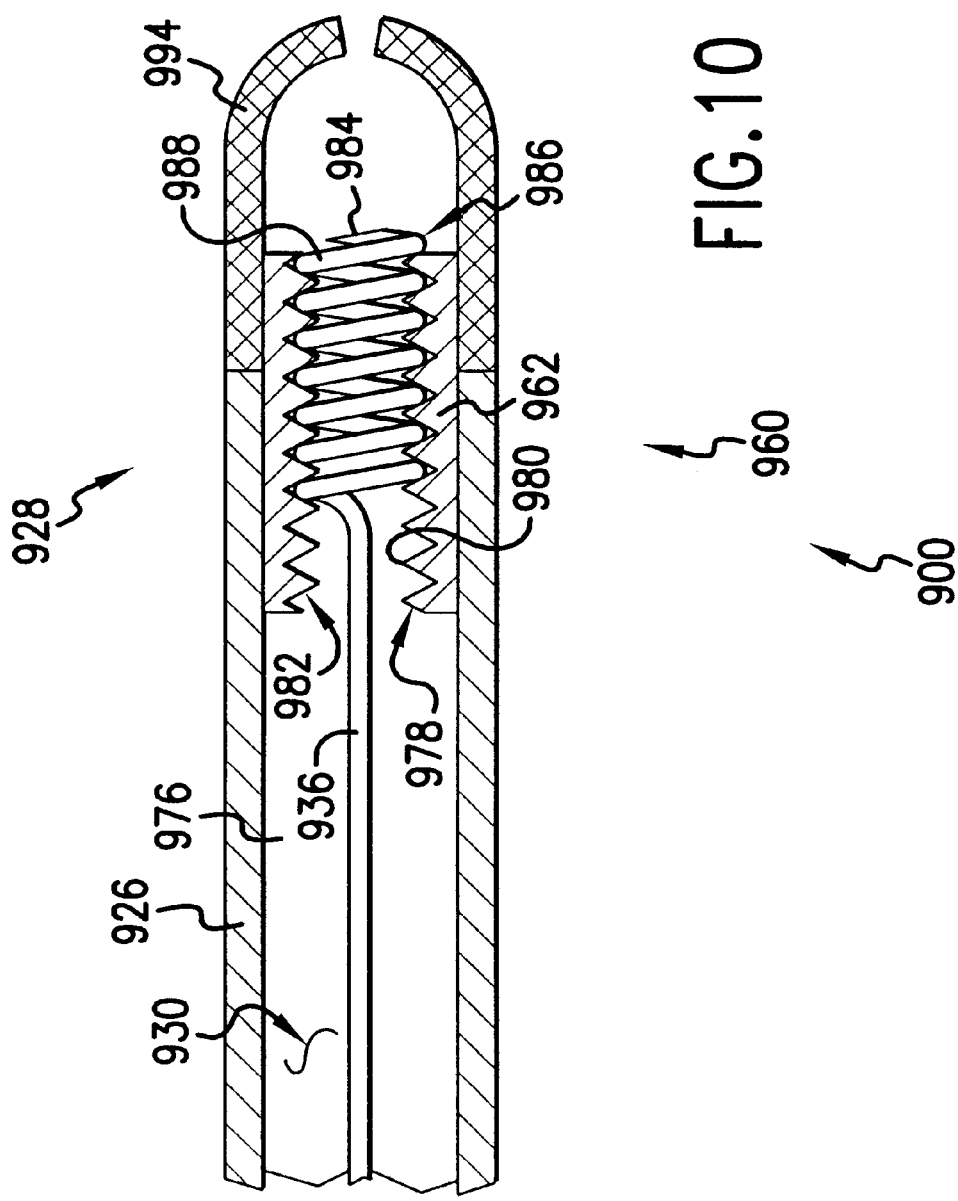
FIG. 10 is a partial cross sectional view of a distal portion of a catheter in accordance with an exemplary embodiment of the present invention.

FIG. 10 is a partial cross sectional view of a distal portion 960 of an additional embodiment of a catheter 900 in accordance with the present invention. Catheter 900 includes a first elongate shaft 926 having a distal end 928 and an inside surface 976 defining a first shaft lumen 930. A tip member 994 is disposed proximate distal end 928 of first elongate shaft 926. In a preferred embodiment, tip member 994 is comprised of an elastomeric material.

A barrel 962 is partially disposed within first shaft lumen 930 of first elongate shaft 926 proximate tip member 994. Barrel 962 includes a first helical member 978 comprising a plurality of turns 980. In the embodiment of FIG. 10, first helical member 978 comprises a first screw thread 982. A second elongate shaft 936 is partially disposed within first shaft lumen 930 of first elongate shaft 926. Second elongate shaft 936 forms a second helical member 984. In the embodiment of FIG. 10, second helical member 984 comprises a coil 986 having a plurality of turns 988. In FIG. 10, it may be appreciated that a plurality of turns 988 of second helical member 984 are disposed between a plurality of turns 980 of first helical member 978.

Figure 11:
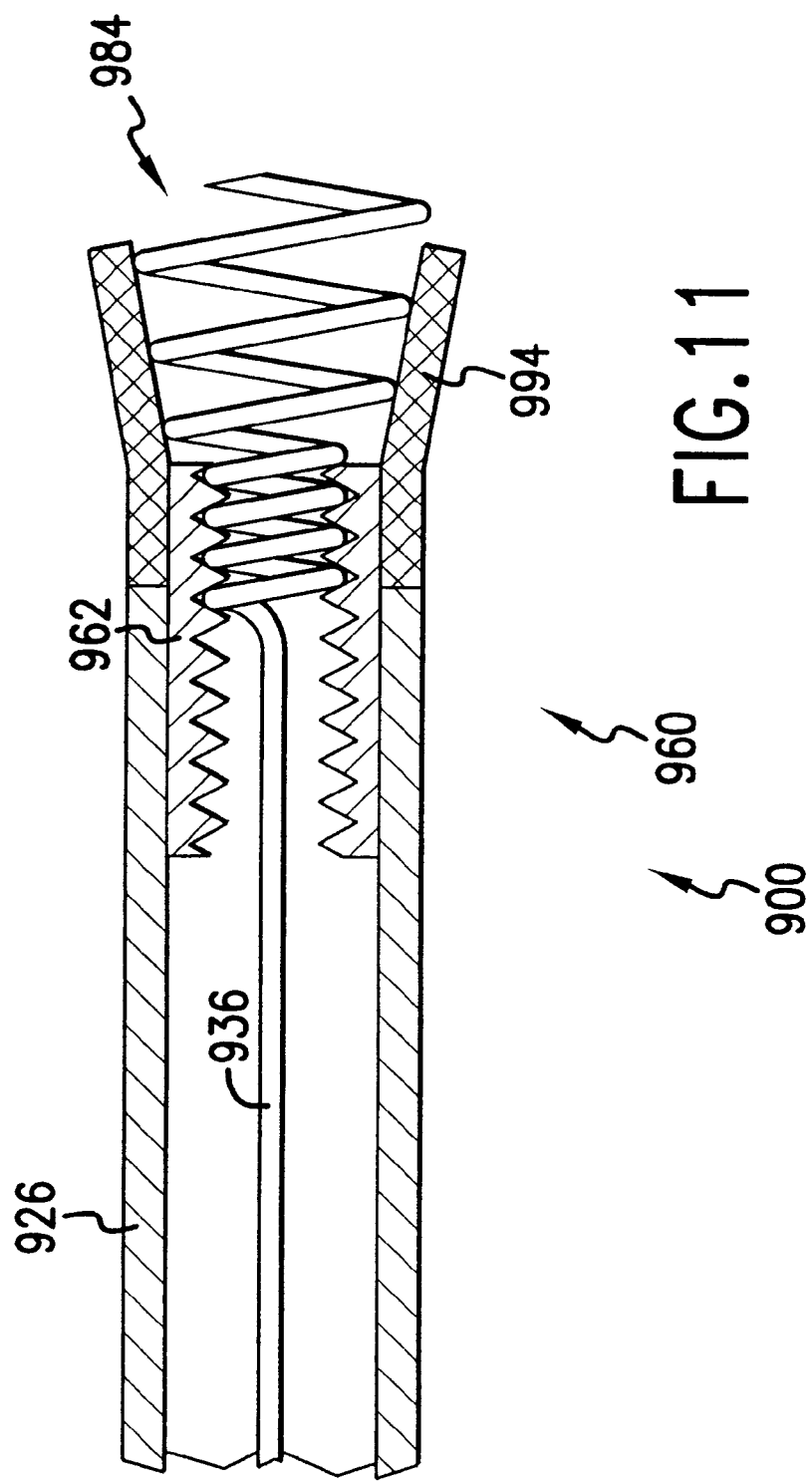
FIG. 11 is a partial cross sectional view of an additional embodiment of the catheter of FIG. 10.

FIG. 11 is a partial cross sectional view of distal portion 960 of catheter 900 of FIG. 10. In the embodiment of FIG. 11 second elongate shaft 936 has been advanced distally so that a distal portion of second elongate shaft 936 extends beyond barrel 962. In FIG. 11, it may be appreciated that second helical member 984 is biased to expand in diameter. Also in FIG. 11, it may be appreciated that the expansion of second helical member 984 has deformed tip member 994.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A catheter comprising:
   a first elongated shaft,
      the first elongated shaft defining a lumen,
      the first elongated shaft having a longitudinal axis,
      the first elongated shaft having a proximal end and a distal end,
      the distal end having a point;
   a housing surrounding at least a portion of the first elongated shaft,
      the housing having a proximal end and a distal end,
      the distal end having a distal contact area; and
   a barrel coupled to the distal end of the housing and the barrel defining the distal contact area,
   the first elongated shaft slidable within the housing from a first position to a second position,
   the longitudinal axis of the distal end of the first elongated shaft defining a curve when the distal end is in the second position.

2. The catheter of claim 1 wherein the longitudinal axis of the distal end of the first elongated shaft defines a straight line when in the first position.

3. The catheter of claim 1 further comprising:
   a second elongated shaft,
      the second elongated shaft defining a lumen,
      the second elongated shaft having a longitudinal axis,
      the second elongated shaft having a proximal end and a distal end,
      the second elongated shaft slidable within the first elongated shaft from a first position to a second position,
      the second position locating the distal end of the second elongated shaft outside of the distal end of the first elongated shaft.

4. The catheter of claim 3 wherein the longitudinal axis of the second elongated shaft defines a line when the second elongated shaft is in the first position and defines a curve when the shaft is in the second position.

5. The catheter of claim 1 wherein the curve is in the form of a first helix.

6. The catheter of claim 1 wherein an internal surface of the barrel defines a screw thread.

7. The catheter of claim 5 wherein the longitudinal axis of the distal end of the first elongated shaft is in the form of a second helix when the distal end is in the first position.

8. The catheter of claim 6 wherein the form of the first helix is more tightly wound than the form of the second helix.

9. The catheter of claim 1 further comprising:
   a screw and thread mechanism coupling the first elongated shaft with the housing.

10. The catheter of claim 1 wherein a portion of the longitudinal axis of the proximal end of the first elongated shaft is in the form of a helix.

11. The catheter of claim 1 wherein the distal contact area is moveable from a first closed position to a second open position, the first closed position having the distal contact area orientated towards the longitudinal axis of the first elongated shaft.

12. A catheter comprising:

a first elongated shaft,
the first elongated shaft defining a lumen,
the first elongated shaft having a longitudinal axis,
the first elongated shaft having a proximal end and a distal end, a housing surrounding at least a portion of the first elongated shaft,
the housing having a proximal end and a distal end,
the distal end having a distal contact area; and a barrel coupled to the distal end of the housing and the barrel defining the distal contact area, the first elongated shaft slidable within the housing from a first position to a second position, the longitudinal axis of the distal end of the first elongated shaft defining a curve when the distal end is in the second position.

13. The catheter of claim 12 wherein the longitudinal axis of the distal end of the first elongated shaft defines a straight line when in the first position.

14. The catheter of claim 12 further comprising:

a second elongated shaft,
the second elongated shaft defining a lumen,
the second elongated shaft having a longitudinal axis,
the second elongated shaft having a proximal end and a distal end,
the distal end having a point,
the second elongated shaft slidable within the first elongated shaft from a first position to a second position,
the second position locating the distal end of the second elongated shaft outside of the distal end of the first elongated shaft.

15. The catheter of claim 14 wherein the longitudinal axis of the second elongated shaft defines a line when the second elongated shaft is in the first position and defines a curve when the shaft is in the second position.

16. The catheter of claim 12 wherein the curve is in the form of a first helix.

17. The catheter of claim 12 wherein an internal surface of the barrel defines a screw thread.

18. The catheter of claim 16 wherein the longitudinal axis of the distal end of the first elongated shaft is in the form of a second helix when the distal end is in the first position.

19. The catheter of claim 17 wherein the form of the first helix is more tightly wound than the form of the second helix.

20. The catheter of claim 12 further comprising:

a screw and thread mechanism coupling the first elongated shaft with the housing.

21. The catheter of claim 12 wherein a portion of the longitudinal axis of the proximal end of the first elongated shaft is in the form of a helix.

22. The catheter of claim 12 wherein the distal contact area is moveable from a first closed position to a second open position, the first closed position having the distal contact area orientated towards the longitudinal axis of the first elongated shaft.

* * * * *